US00PP14115P29

(12) United States Plant Patent
Lemon

(10) Patent No.: US PP14,115 P2
(45) Date of Patent: Aug. 26, 2003

(54) GERANIUM PLANT NAMED 'GLOBAL RED'

(75) Inventor: David Lemon, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 10/245,524

(22) Filed: Sep. 17, 2002

(51) Int. Cl.[7] ..... A01H 5/00

(52) U.S. Cl. ..... Plt./332

(58) Field of Search ..... Plt./332

*Primary Examiner*—Kent Bell
(74) *Attorney, Agent, or Firm*—Webb Ziesenheim Logsdon Orkin & Hanson, P.C.

(57) ABSTRACT

A new and distinct ivy geranium plant with distinctive red colored flowers above emerald green foliage. The new variety has excellent heat tolerance and flowers that do not burn in bright sunlight.

1 Drawing Sheet

Botanical classification: *Pelargonium×peltatum* (ivy geranium).
Varietal denomination: 'Global Red'.

BACKGROUND OF THE INVENTION

The present invention comprises a new and distinct cultivar of *Pelargonium×peltatum* known by the varietal name 'Global Red'. The new variety was discovered in a selected breeding program in Lompoc, Calif. as Breeder No. 6DG3595-1. The new variety is a result of cross breeding of 'Nicole' (female) (U.S. Plant Pat. No. 7,358) and 'Global Ruby Red' (male) (U.S. Plant Pat. No. 11,600). The new variety exhibits similar plant type to both parents. The flower color is redder than 'Nicole' (pink) and is a lighter color than 'Global Ruby Red'. The new variety was first asexually reproduced by cuttings in Connellsville, Pa. The new variety has been trial and field tested at Connellsville and has been found to retain its distinctive characteristics and remain true to type through successive propagations.

The cultivar, when grown in a glass greenhouse in Connellsville, Pa. using natural light and temperatures of 60° F. night and 68° F. day, has a response time of 12 weeks from a rooted cutting to flowering in a 10 inch pot. The response time was determined on plants grown in soilless media employing constant fertilizer 200–250 parts per million of nitrogen and potassium in full light. Three cuttings planted in a pot and pinched at four weeks produce a finished hanging basket.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected by asexual reproductions carried out by Oglevee, Ltd. in Connellsville, Pa. Plants were about 12 weeks old when described. The color readings were taken on a plant under 65–85 foot candles of fluorescent cool white light. Color references are primarily to The R.H.S. Colour Chart of The Royal Horticultural Society of London.

PLANT

Form: Compact, cascading mound.
Height: 18 cm from media surface to top of foliage in a 6 inch pot.
Diameter: 45 cm.
Strength: Does not require artificial support.
Rooting time: Roots visible to outside of a dirt plug in 10–14 days.
Leaves:
- *Attachment.*—Alternate.
- *Stipules.*—Two per node.
- *Size.*—Length: 4.0–5.25 cm. Width: 6.0–7.0 cm. Zone: 5–7 mm from petiole attachment; zone is 7 mm wide.
- *Shape.*—Reniform; cordate base, pointed apex.
- *Margin.*—Entire with lobes.
- *Texture.*—Leathery.
- *Pubescence.*—Slight.
- *Color.*—Upper surface: 137B. Lower surface: 137C. Zone: Noticeable on leaves in range of intensity from 187A to 147A.
- *Ribs and veins.*—Venation: Palmate. Color: 146C.

Petioles:
- *Color.*—146B.
- *Length.*—4.0–6.0 cm.

Stem:
- *Color.*—146B.
- *Length.*—25 cm.
- *Internode length.*—2.0–4.5 cm.

THE BUD

Shape when no color showing:
- *Overall.*—Elongated, elliptical cluster.
- *Individual bud.*—Elliptical or oval.

Size when no color showing:
- *Overall.*—3.0–4.0 cm across cluster.
- *Individual bud.*—0.4–0.6 cm wide; 1.1–1.4 cm long.

Number of buds per cluster: 6–9.
Color (Just prior to sepals parting at tips): 46B at petal edge and 155B.

INFLORESCENCE

Blooming habit: Continuous flowering; throughout growing season.

Size of umbel: 8–10 cm in diameter, 6 cm in depth.

Borne: Umbel, flowers on pedicel, pedicel on peduncle, 5.0–8.0 cm above foliage.

Flowers:

*Form.*—Slightly cupped.

*Number of flowers per umbel.*—6–9.

*Size.*—Diameter: 4.8–5.4 cm. Depth: 0.8–1.1 cm.

Petals:

*Color.*—Upper surface: 2–3 upper petals have an eye and the lower petals are without an eye. Petals with an eye exhibit 46B at the outer edge with areas of 46A. Near the low middle of the petal there is venation of 71A fading to 71C then to white, 155D. At the base of the petal, thick venation of 71A continues then drastically fades to white, 155D. Petals without an eye exhibit 46B at the outer edge with areas of 46A. At the base, the color blends quickly into 42A and then fades to white, 155D. There is a faint venation of 71A present in the petal. Lower surface: The outer edges begin as 46B and fade quickly to 46D. As 46B fades to 46D there begins white speckling, 155D, and the intensity of the speckles increases steadily to the center of the petal where the color is solid white, 155D. The venation shows through from the front. Shape: Inverted teardrop; pointed base, rounded apex. Size: 2.7–3.1 cm long; 1.7–2.2 cm wide. Margin: Entire. Number per flower: 10–15. Texture and appearance: Highly reflective, smooth, velvety.

Tonality from a distance: Ruby red, velvety flowers with white eyes standing atop cascading emerald green foliage.

Petaloids:

*Quantity.*—0–5.

*Shape.*—Irregular; some twisted; tubular.

*Color.*—Same as petals.

Sepals:

*Quantity.*—5.

*Shape.*—Narrow; nearly parallel at base, narrows to point; pointed apex, entire margin.

*Size.*—1.4–1.5 cm long; 0.3–0.6 cm wide.

*Color.*—Upper and Lower Surface: 144B.

Pedicel:

*Length*—1.8–2.6 cm.

*Color.*—144A with anthocyanin staining 183B on some older pedicels.

Peduncle:

*Length.*—9–15 cm.

*Color.*—144A.

Lasting quality: Umbels last 7–14 days; individual flowers last 7 days.

Disease/pest resistance: No susceptibility to diseases or pests has been noted to date.

REPRODUCTIVE ORGANS

Stamens:

*Anthers.*—2 mm in length.

*Filaments.*—Length: 0.9–1 cm. Color: White with some reddening. Pollen: Rusty orange.

Pistils:

*Number.*—One.

*Length.*—1.1–1.2 cm.

*Stigma.*—Number: One. Color: Deep purple.

*Style.*—Length: 3–4 mm. Color: White.

*Ovaries.*—Superior, thick pubescence, 0.6 cm long, 0.2 cm wide, light green.

Fruit: None observed.

I claim:

1. A new and distinct variety of geranium plant substantially as shown and described.

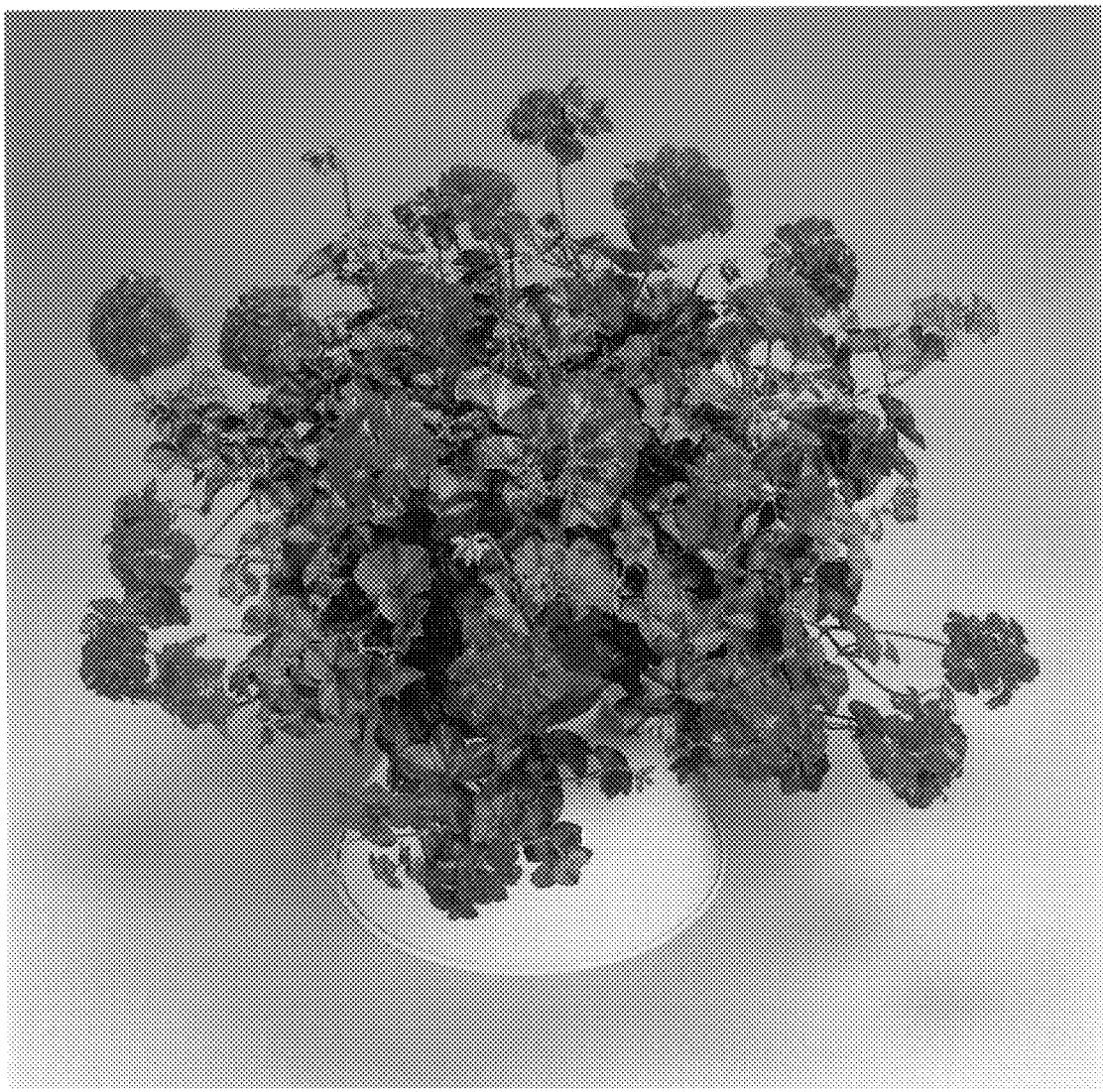

* * * * *